United States Patent [19]

San Miguel et al.

[11] 4,155,653
[45] May 22, 1979

[54] SMOKE-MEASURING TRANSDUCER

[75] Inventors: Anthony San Miguel; James L. Rieger, both of Ridgecrest, Calif.

[73] Assignee: The United States of America as represented by the Secretary of the Navy, Washington, D.C.

[21] Appl. No.: 842,023

[22] Filed: Oct. 14, 1977

[51] Int. Cl.² .................................................. G01N 21/28
[52] U.S. Cl. ....................................... 356/438; 250/564; 250/573; 340/630
[58] Field of Search .................. 356/207, 43; 340/628, 340/630; 250/554, 564, 573

[56] References Cited

U.S. PATENT DOCUMENTS

| | | | |
|---|---|---|---|
| 2,966,092 | 12/1960 | Hartridge | 83/14 |
| 3,590,327 | 6/1971 | Thomae | 361/386 X |
| 3,659,278 | 4/1972 | Jensen | 250/577 X |
| 3,760,395 | 9/1973 | Müller | 356/207 |
| 3,790,289 | 2/1974 | Schmidt | 356/205 |
| 3,838,925 | 10/1974 | Marks | 356/207 |
| 3,850,529 | 11/1974 | Brugger | 356/207 |
| 3,874,795 | 4/1975 | Packham et al. | 356/104 |
| 3,885,162 | 5/1975 | Geertz | 250/573 |
| 3,922,655 | 11/1975 | Lecuyer | 340/237 S |

FOREIGN PATENT DOCUMENTS 570017  11/1975  Switzerland ............................ 356/207

Primary Examiner—John K. Corbin
Assistant Examiner—Bruce Y. Arnold
Attorney, Agent, or Firm—R. S. Sciascia; W. Thom Skeer

[57] ABSTRACT

A smoke transducer having an integral photo-electric optical system and heat isolated circuitry. A calibration wedge is designed to permit field calibration and to structurally interfit within the sampling chamber.

31 Claims, 4 Drawing Figures

SMOKE-MEASURING TRANSDUCER

BACKGROUND OF THE INVENTION

1. Field of the Invention

This invention pertains to electrical instrumentation. More specifically, this invention pertains to electro-optical instrumentation. In greater particularity, this invention pertains to photo-electric analysis of gas mixtures. By way of further characterization this invention concerns photo-electric smoke transducers. In still greater particularity this invention will be described as it relates to smoke transducers for aircraft cockpit interiors.

2. Description of the Prior Art

The design of modern aircraft and other vehicles requires the application of many disciplines. In order to make the vehicle as safe as possible, consideration must be given to fire hazards and the possibility of escape in the event of fire. A major problem exists in configuring and placing vital instruments and operational controls where they may be located and seen by operational personnel in the event of fire and the attendant reduction in visibility caused by smoke and heat turbulence. In the close confines of a military aircraft or a naval vessel it is necessary, therefore, to know the density of smoke as a function of time-after-ignition at various points in the vehicle interior. With this knowledge, vital instruments and controls may be placed in locations affording the longest time of visibility thereby facilitating escape and survival of operational personnel.

Of course, in the optical instrumentation arts the photo-electric measurement of smoke and gas turbulency has become commonplace and a well defined subclass of instruments are known for this purpose. However, these instruments are generally large and permanently installed in fixed positions. For effective use in smoke and atmospheric measurements in confined spaces, a transducer must effectively sample a small portion of the ambient space without either responding to other portions of the volume or inhibiting the normal gas flow within the volume. Heretofore, no instrument was sufficiently small, responsive to a limited portion of a larger volume, and heat resistant enough to reliably gather data for vehicle fires.

SUMMARY OF THE INVENTION

A smoke measuring transducer according to the invention uses a compactly dimensioned chamber open at either end to freely communicate with the ambient atmosphere without adversely affecting the gas flow within the ambient atmosphere. The chamber is made of a heat resistant material to facilitate reuse.

Smoke measurement is accomplished by photo-electric detection of a light beam passing through the chamber. Calibration against standard transmissivity is provided by a fixed filter standard. Voltage supply to the light source provides an alternating current to facilitate electrical signal processing without the use of episcotisters. Heat insulation and a gas tight housing protect circuit components from the heat of the vehicle fires and provide for ready repair and reuse.

DESCRIPTION OF THE PREFERRED EMBODIMENT

Figure 1:
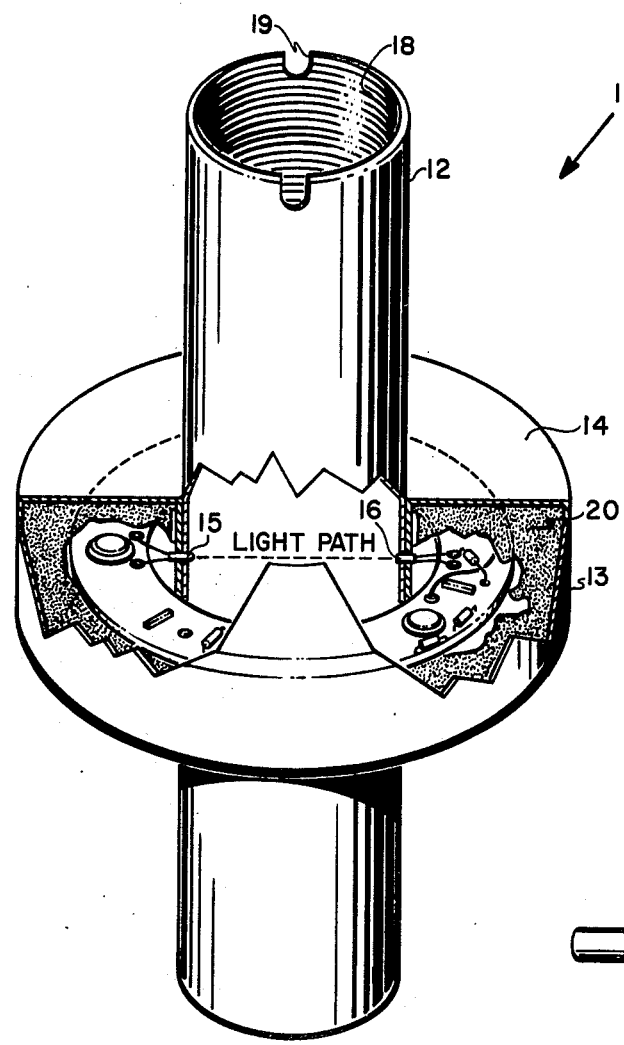
FIG. 1 is a front perspective view, partially cut away, of the transducer of the invention.

Referring to FIG. 1, the smoke transducer of the invention is indicated generally at 11. As shown, smoke transducer 11 includes a tubular chamber 12 having open ends communicating with the ambient atmosphere. Cylinder 12 is fabricated from a suitable heat resistant material capable of withstanding cockpit and other vehicular fires such that multiple uses of the transducer may be had after suitable refurbishing. For example, the body portions of transducer 11 may be made of brass. An annular container 13 is placed about the cylinder 12 in the vicinity of the midportion thereof and is closed by a suitable fitted lid 14.

Container 13 is joined to cylinder 12 for support thereby to establish a unitary construction. For example, the brass fabrication used in developmental models may use pressfit or riveting type attachments in dependence upon well understood engineering tradeoffs.

A suitable source of optical energy, indicated at 15, is positioned to extend through the lateral walls of cylinder 12 and communicate with the interior of container 13. Light source 15 may, for example, be a light emitting diode. A photo detector 16 is positioned diametrically opposite light source 15 to establish a light path extending across the interior of cylinder 12.

An annular circuit board 17 provides mounting support for circuit components, to be described in greater detail herein. These circuit components are used in conjunction with light source 15 and photodetector 16.

The interior of cylinder 12 is treated to reduce optical reflections from the walls thereof such that light external to transducer 11 exerts a minimum influence of the system. A variety of optical antireflection coatings are known in the art and their use for this purpose is conventional and, therefore, selection as between the various antireflection treating techniques is left to the discretion of the user. However, it should be noted that the reflection reducing treatment should not in itself be susceptible of producing smoke or other atmospheric pollutants which would affect the validity of the measurements.

One end of cylinder 12 is provided with notches 19. Notches 19 are placed so as to support an optical calibration filter in the light path extending between light source 15 and photodetector 16. Thus, notches 19 constitute retaining means specifically adapted to cooperate with support means on said optical filter to be described.

In order to promote longevity in the arduous environment to which transducer 11 is exposed, and to preserve the circuitry mounted upon circuit board 17, the void within container 13 not occupied by circuit board 17 and the components mounted thereon are filled with a suitable particulate insulating material. This material is chosen to provide maximum heat insulation for the circuit board and to additionally provide support therefor. A particulate type insulator is preferred in order to facilitate removal of circuit board 17 for repair and refurbishing. In developmental models of the invention, diatomaceous earth has been used for this material and is indicated generally at 20.

Figure 2:
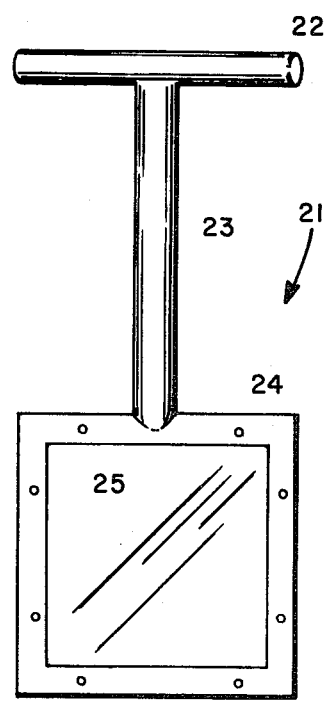
FIG. 2 is a perspective view of a calibration filter.

Referring to FIG. 2, an optical calibration filter is illustrated generally at 21. As shown, filter 21 includes a transverse rod 22 having a longitudinal rod 23 depending from the mid portion thereof. A frame 24 is supported by rod 23 and surrounds an optical filter 25 having a predetermined optical attenuation which is within the operational range of transducer 11. This attenuation is chosen such that calibration thereof may be checked after installation in the vehicle.

Figure 3:
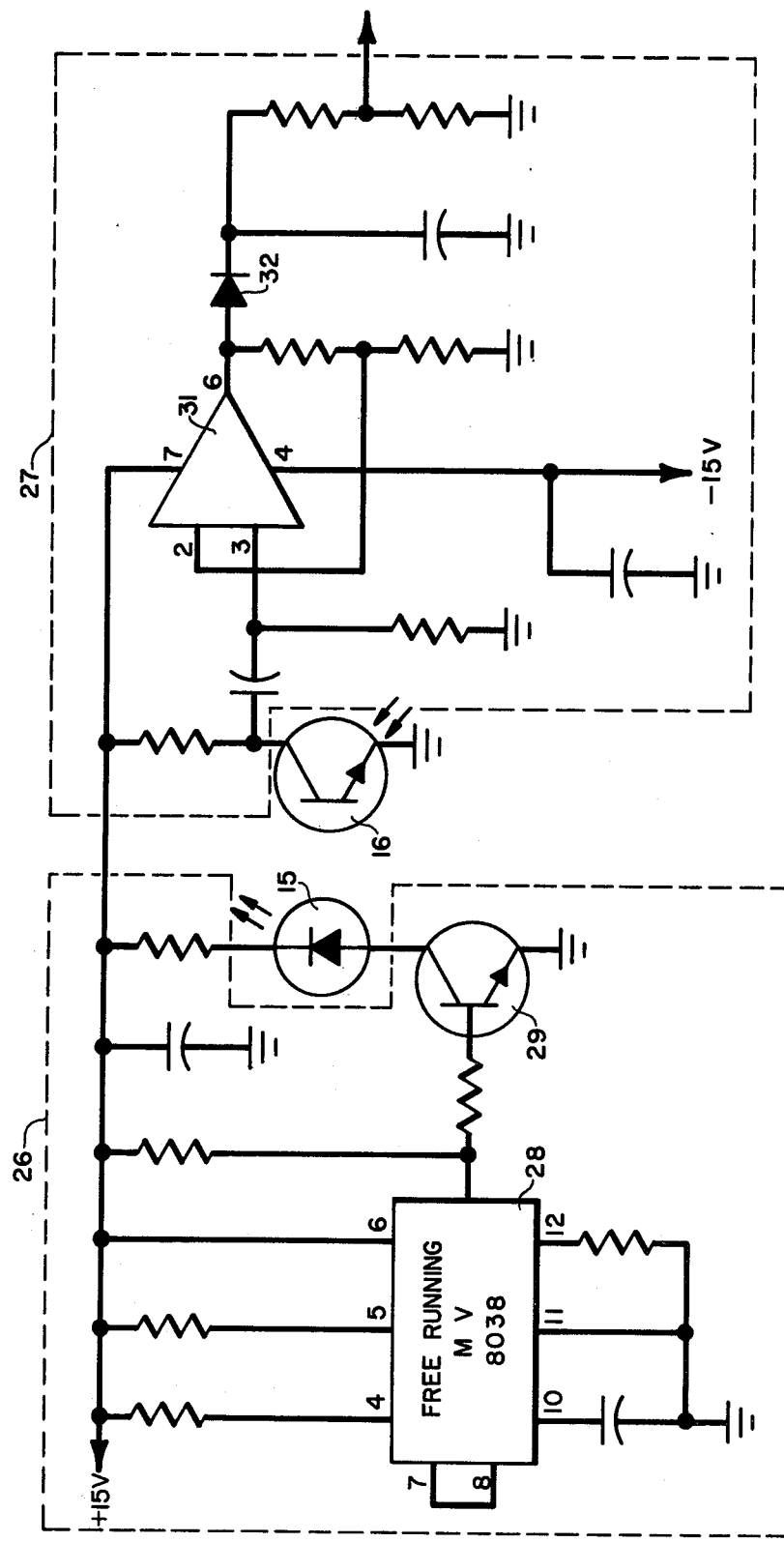
FIG. 3 is a circuit diagram of the electrical circuit according to the invention.
Figure 4:
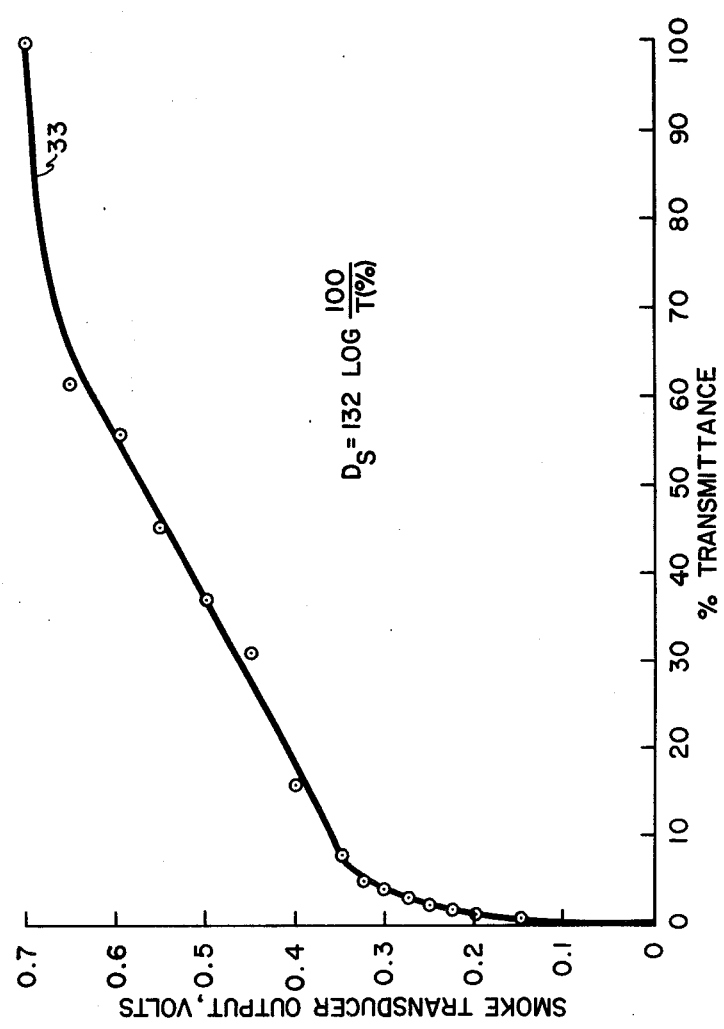
FIG. 4 is a graph showing the output of the transducer in comparison with a standard curve.

Referring to FIG. 3, the circuit components are shown in a schematic interconnection indicating an operational configuration found advantageous in developmental models. A first circuit 26 provides for means first supplying a voltage to light source 15 and, similarly, circuit 27 provides second means connected to photodetector 16 for processing the electrical output therefrom.

Circuit 26 has as a principle element an integrated circuit 28 which is connected to form a free running multivibrator. Although a variety of such circuits are known, that marketed under the trade designation 8038 has proven particularly satisfactory in the development of the invention. The output of free running multivibrator 28 is a square wave with a 50% duty cycle which is used to operate a solid state switch indicated at 29 such that the light output from light emitting diode 15, which serves as a light source, is a series of pulses rather than a continuous optical output. The advantages of interrupted signals are what is well known in the smoke and gas turbidity measuring arts. In the invention, the pulses serve the conventional functions and provide a tunable signal which may be easily distinguished from background radiation and other noise sources. Customarily, this function is provided by a mechanical shutter. However due to the requirements of compactness and temperature resistance, the illustrated arrangement has marked advantages.

Photodetector 16 is illustrated as a photo transistor and is positioned to receive the pulsed light from light emitting diode 15. The electrical analog produced by photodetector 16 is a series of pulses diminished in amplitude by the absorption of light energy by smoke within chamber 12. This alternating series of pulses is connected by a suitable coupling resistor and capacitor network to an operational amplifier 31. Operational amplifier 31 may be of any type known in the art which incorporates the desired operational characteristics of linearly and response range. In developmental models, the type of operational amplifier marketed under the trade designator $\mu$A741 has proven satisfactory for operational amplifier 31.

The amplified output of operational amplifier 31 is rectified, or detected, by diode 32 and is stored or smoothed into a dc response voltage by means of a resistor capacitor network attached thereto.

The illustrated circuit, may be calibrated against the standard for smoke density developed at the National Bureau of Standards which has served as a standard for measuring smoke characteristics of smoke producing materials for a number of years. For a further discussion of the standards, see the Natonal Bureau of Standards Technical Note No. 757 entitled "The Smoke Density Chamber Method for Evaluating the Potential Smoke Generation of Building Materials" by T. G. Lang issued by the National Bureau of Standards, Washington, D. C. in January 1973.

As shown in FIG. 3, the performance figures obtained from the transducer of the invention, illustrated at the various dots, closely matches the Bureau of Standards curve given at 33 and represented by the formula $Ds = 132 \log(100/T)$ where: Ds is described as the specific optical density and T is the percent of light transmission.

In operation, transducer 11 is placed within the vehicle to be tested, the appropriate power mains are connected thereto, as well as the recording instruments to record the output voltage therefrom, and the operation is checked by inserting test filter 21 within cylinder 12 where it is held by means of notches 19 interacting with rod 22. The operational parameters, including the supply voltage, may be then adjusted such that the predetermined operational conditions are obtained. Filter 21 is removed. The combustion within the vehicle is then ignited and a time measurement of optical transmission or smoke density is made with respect to the time of ignition of the fire. At the conclusion of a predetermined test period, which for some applications is the duration at which it has been determined that an occupant of the vehicle is likely to survive, the fire is extinguished and the tranducer 11 retrieved for refurbishment such that it may be used in successive tests.

Thus, it may be seen the foregoing description taken with the appended claims constitute a disclosure such as to enable a person skilled the electronics and optical instrumentation arts and having the benefit of the teachings contained therein to make and use the invention. Further, the invention herein described is seen to generally constitute a meritorious advance in the art unobvious to such a worker not having the benefit of these teachings.

What is claimed is:

1. A smoke detector comprising:

a chamber connunicating with an external environment in which smoke may be present and having lateral walls dimensioned to sample a representative volume of said environment and configured to admit gas therein without contributing to gas flow within the environment;

a light source extending through a lateral wall of said chamber;

a photodetector means extending through a lateral wall of said chamber and positioned in optical alignment with said light source to receive the light output therefrom for producing an electrical analog thereof;

first means electrically connected to said light source for supplying a predetermined voltage thereto;

second means electrically connected to said photodetector means for processing said electrical analog to produce an electrical output indicative of a standard smoke density curve; and thermal insulation means within a container which is connected to the lateral walls of said chamber so as to partially enclose said light source and said photodetector, and to effectively enclose said first means, and said second means for protecting them from said external environment.

2. A smoke detector according to claim 1 in which said lateral walls of said chamber are configured to reduce light reflection therefrom.

3. A smoke detector according to claim 1 in which said light source is a light emitting diode.

4. A smoke detector according to claim 1 in which said first means is an electrical square wave source.

5. A smoke detector according to claim 4 in which said electrical square wave oscillator has a 50% duty cycle.

6. A smoke detector according to claim 1 in which said source means includes an alternating current amplifier.

7. A smoke detector according to claim 1 in which said insulation means includes a particulate insulation material.

8. A smoke detector according to claim 7 in which said insulation material is diatomaceous earth.

9. A smoke detector according to claim 1 further including:
an annular circuit mounting connected to said first and second means and positioned to extend circumferentially about said chamber.

10. A transducer for smoke measurement in a high temperature environment comprising:
a cylinderically shaped chamber made of heat resistant material and having open ends to communicate with the surrounding environment;
optical means mounted on said cylindrically shaped chamber for establishing an optical beam extending thereacross, said optical means including,
a light source, and
a light responsive detector;
an electrical circuit connected to said optical means for supplying electrical energy thereto to enable light generation and detection thereby, said electrical circuit including a circuit board which extends circumferentially about the exterior of said cylindrically shaped chamber;
an enclosure having walls made of heat resistant material attached to said cylindrically shaped chamber and positioned to enclose said electrical circuit within the interior thereof having dimensions to provide interior space in excess of that required for said electrical circuit; and
thermal insulation filling the interior space of said enclosure not occupied by said electrical circuit, and contacting the circuit board thereof to support the circuit board in a spaced relation to said enclosure walls.

11. A transducer according to claim 10 further comprising:
a calibration filter having a predetermined transmission and configured to be placed within said cylinderical chamber to be positioned within said optical beam; and
indexing means on said cylinderically shaped chamber for receiving said calibration filter, and for supporting it in an operative position in said optical beam so as to provide a reference transmission attenuation therefor.

12. A smoke detector comprising:
a chamber communicating with an external environment in which smoke may be present and having lateral walls dimensioned to sample a representative volume of said environment without contributing to gas flow within the environment;
a light source having a portion extending through a later wall of said chamber; a photodetector means having a portion thereof extending through a lateral wall of said chamber and positioned in optical communication with said light source to receive the light output therefrom for producing an electrical analog thereof;
first means electrically connected to said light source for supplying a predetermined voltage thereto;
second means electrically connected to said photodetector means for processing said electrical analog to produce an electrical output;
thermal insulation means within a container which is connected to the lateral walls of said chamber so as to substantially enclose the portions of said light source and said photodetector not extending through a lateral wall, and enclosing said first means and said second means for protecting them from said external environment;
an optical filter dimensioned to fit within said chamber;
support means attached to said optical filter for positioning said filter at a predetermined position within said chamber so as to intercept light passing between said light source and said photodetector; and
retaining means on said chamber configured to engage said support means for establishing a calibration position for said optical filter and attached support means.

13. A smoke detector according to claim 12 in which said optical filter is a neutral density filter having a predetermined transmission.

14. A smoke detector according to claim 12 in which said support means includes:
an elongated member joined to said optical filter; and
a transverse member joined to said elongated member at right angles thereto.

15. a smoke detector according to claim 14 in which the aforesaid retaining means engages said transverse member.

16. A smoke detector according to claim 15 in which the aforesaid retaining means includes diametrically spaced notches in the lateral walls of the aforesaid chamber.

17. A smoke detector according to claim 12 in which said lateral walls of said chamber are configured to reduce light reflection therefrom.

18. A smoke detector according to claim 12 in which said light source is a light emitting diode.

19. A smoke detector according to claim 12 in which said first means is an electrical square wave source.

20. A smoke detector according to claim 19 in which said electrical square wave oscillator has a 50% duty cycle.

21. A smoke detector according to claim 12 in which said source means includes an alternating current amplifier.

22. A smoke detector according to claim 12 in which said thermal insulation means includes a particulate insulation material.

23. A smoke detector according to claim 22 in which said insulation material is diatomaceous earth.

24. A smoke detector comprising:
a chamber communicating with an external environment in which smoke may be present and having lateral walls dimensioned to sample a representative volume of said environment without contributing to gas flow within the environment;
a light source extending through a lateral wall of said chamber;
a photodetector means extending through a lateral wall of said chamber and positioned in optical communication with said light source to receive the light output therefrom for producing an electrical analog thereof;

first means electrically connected to said light source for supplying a predetermined voltage thereto;

second means electrically connected to said photodetector means for processing said electrical analog to produce an electrical output;

an annular circuit mounting means connected to said first and second means for providing a mounting therefor and positioned such that the lateral walls of said chamber extend through the center thereof; and thermal insulation means within a container which is connected to the lateral walls of said chamber so as to enclose and support said annular circuit mounting means.

25. A smoke detector according to claim 24 in which said lateral walls of said chamber are configured to reduce light reflection therefrom.

26. A smoke detector according to claim 24 in which said light source is a light emitting diode.

27. A smoke detector according to claim 24 in which said first means is an electrical square wave source.

28. A smoke detector according to claim 27 in which said electrical square wave oscillator has a 50% duty cycle.

29. A smoke detector according to claim 24 in which said source means includes an alternating current amplifier.

30. A smoke detector according to claim 24 in which said thermal insulation means includes a particulate insulation material.

31. A smoke detector according to claim 24 in which said thermal insulation means is diatomaceous earth.

* * * * *